US008399229B2

United States Patent
Sooryakumar et al.

(10) Patent No.: US 8,399,229 B2
(45) Date of Patent: Mar. 19, 2013

(54) MOBILE MAGNETIC TRAPS AND PLATFORMS FOR MICRO/NANO PARTICLE MANIPULATION

(75) Inventors: Ratnasingham Sooryakumar, Columbus, OH (US); Dhriti Sooryakumar, Columbus, OH (US); Gregory Vieira, Columbus, OH (US); Jeffrey J. Chalmers, Columbus, OH (US)

(73) Assignee: The Ohio State University, Columbus, OH (US)

( * ) Notice: Subject to any disclaimer, the term of this patent is extended or adjusted under 35 U.S.C. 154(b) by 269 days.

(21) Appl. No.: 12/950,130

(22) Filed: Nov. 19, 2010

(65) Prior Publication Data

US 2011/0124077 A1 May 26, 2011

Related U.S. Application Data

(63) Continuation of application No. PCT/US2009/045011, filed on May 22, 2009.

(60) Provisional application No. 61/055,263, filed on May 22, 2008.

(51) Int. Cl.
*B03C 1/035* (2006.01)
(52) U.S. Cl. .......... 435/173.9; 435/283.1; 210/222; 210/695; 977/762; 422/552
(58) Field of Classification Search .......... 435/173.9, 435/283.1, 287.2; 210/222, 695; 422/552; 977/762
See application file for complete search history.

(56) References Cited

U.S. PATENT DOCUMENTS

| | | | |
|---|---|---|---|
| 3,808,550 A | 4/1974 | Ashkin | |
| 4,170,447 A | 10/1979 | Goldstein et al. | |
| 5,017,789 A | 5/1991 | Young et al. | |
| 5,814,200 A | 9/1998 | Pethig et al. | |
| 7,267,999 B2 | 9/2007 | Drewes | |
| 2003/0144720 A1 | 7/2003 | Villaseca et al. | |
| 2004/0262210 A1 | 12/2004 | Westervelt et al. | |
| 2006/0073540 A1 | 4/2006 | Martel | |
| 2007/0141728 A1* | 6/2007 | Moreland et al. | 436/526 |
| 2007/0182517 A1 | 8/2007 | Humphries et al. | |
| 2008/0124779 A1 | 5/2008 | Oh et al. | |
| 2008/0176762 A1 | 7/2008 | Herold et al. | |

OTHER PUBLICATIONS

Berger et al. 2001. Design of a microfabricated magnetic cell separator. Electrophoresis, vol. 22, pp. 3883-3892.*
Dexter Magnetic Technologies, http://www.dextermag.com/about-us/history, Printed Oct. 13, 2012.*
Kläui et al., Direct Observation of Domain-Wall Configurations Transformed by Spin Currents, The American Physical Society, Jul. 8, 2005, pp. 026601-1-026601-4.
Li, et al., Effects of Spin Current on Ferromagnets, Condensed Matter > Materials Science, Article 0508735v1, Aug. 30, 2005, pp. 1-6.

* cited by examiner

*Primary Examiner* — Sally Merkling
(74) *Attorney, Agent, or Firm* — Dinsmore & Shohl LLP

(57) ABSTRACT

Magnetic array platforms such as nano or micro-wire networks that produce trapping, manipulation, and transport of micro- or nano-scale particles such as non-biological entities such as magnetic particles and cells, viruses, DNA, proteins, and other biological entities having magnetic particles labeled or tethered thereto are provided. Methods of manipulating, transporting, and sorting micro- or nano-scale particles are described.

12 Claims, 7 Drawing Sheets

MOBILE MAGNETIC TRAPS AND PLATFORMS FOR MICRO/NANO PARTICLE MANIPULATION

CROSS-REFERENCE TO RELATED APPLICATIONS

This application in a continuation application of International Application No. PCT/US2009/045011, filed May 22, 2009, which claims the benefit of U.S. Provisional Application Ser. No. 61/055,263, filed May 22, 2008.

FIELD OF THE INVENTION

The present invention relates to magnetic array platforms such as nano- or micro-wire networks that produce trapping, manipulation, and transport of micro- or nano-scale non-biological entities such as inert magnetic particles or biological cells, viruses, DNA, proteins, and other biomolecules that have been tethered to or labeled with magnetic particles.

BACKGROUND

Transport, separation and characterization of micro- or nano-scale particles has a wide variety of applications ranging from industrial applications, to biological applications, to environmental applications. For example, in the field of biology, the separation of cells has numerous applications in medicine and biotechnology. Historically, sorting technologies focused on gross physical characteristics, such as particle size or density, or utilized some affinity interaction, such as receptor-ligand interactions or reactions with immunologic targets.

Electromagnetic response properties of materials have been utilized for particle sorting and characterization. For example, dielectrophoretic separators utilize non-uniform DC or AC electric fields for separation of particles. See, e.g., U.S. Pat. No. 5,814,200, Pethig et al., entitled "Apparatus for Separating By Dielectrophoresis."

Coherent light has been used to trap and manipulate particles. One of the earliest workers in the field was Ashkin, U.S. Pat. No. 3,808,550 entitled "Apparatuses for Trapping and Accelerating Neutral Particles" which disclosed systems for trapping or containing particles through radiation pressure. Lasers generating coherent optical radiation were the preferred source of optical pressure.

Other particle manipulation techniques include the use of atomic force microscopy (AFM) or magnetic force microscopy (MFM). An AFM uses a cantilever, sometimes with a receptor attached to the cantilever tip, to identify and manipulate a single cell or protein on a surface by stretching the cell in an out-of-plane direction. Similarly, an MFM utilizes a magnetic field to manipulate and stretch a cell or protein with a magnetic bead attached thereto in an out-of-plane direction.

The sorting of individual cells or micro- or nano-scale particles is an old problem, whether attempting to isolate a single cell or particle, or identifying a specific sub-population of cells or particles that behave differently or have different properties than the rest of the population. While instruments and techniques exist to enable cells or particles to be seen, manipulation of single cells or particles, or groups of them within a larger population, has been problematic.

As noted above, one traditional method of cell manipulation involves laser capture in which cells can be trapped using a laser beam. However, such systems are slow, laser power intensive, and cannot be automated to isolate and manipulate multiple cells. Another traditional method, atomic force microscopy, can be used to identify and manipulate a single cell. However, again, the instrumentation cannot be automated to isolate and manipulate multiple cells. The use of magnetic tweezers has also been tried. However, that technique produces an out-of-plane pulling force on a cell and cannot be automated to isolate and manipulate multiple cells.

Accordingly, the need still exists for a technique which can isolate and trap individuals cells or micro- or nano-scale particles, and then readily manipulate the cells/particles for transport and testing or to separate them from a heterogeneous population. Desirably, such a technique would be able to manipulate thousands or tens of thousands of individual cells or particles in a short period of time.

SUMMARY

Embodiments of the invention provide a magnetic platform, such as a network of wire arrays fabricated on a planar platform, that is used to trap and move micro- and nano-scale particles. By "network of wire arrays," we mean an interconnected system of at least two such wires positioned adjacent one another. An example would be an array of zigzag wires such that the spacing between adjacent arms in the wire varies. Other wire patterns are useful including stair-stepped arrays. In one embodiment, the wires should include one or more non-linear segments such that the spacing between individual wires varies along the respective lengths of such wires and consecutive non-linear segments form a vertex which will function as a magnetic trap. The wires could also be substantially linear with periodically spaced narrowed sections or notches formed therein, the narrowed or notched portions functioning to form magnetic traps. By vertex or vertices, we mean the apex or point at which successive segments of the wire connect. By micro- or nano-wires, we mean wires having widths ranging from about 100 nanometers to about 10 microns. The design and architecture of the network of mobile traps provide the framework for organizing well-defined planar assemblies of these small particles. One feature of this collection of traps is the ability to continuously tune the strength of the trapping potential by a weak (e.g., <500 Oersted) external magnetic field.

As used herein, the term "magnetic trap" means a localized site where a magnetic field traps micron or nano-sized magnetic particles. Such a magnetic field would originate from a domain wall (i.e., an interface separating two magnetic domains) and the resulting effective magnetic field could be tuned with external magnetic fields. The magnetic particles may comprise any suitable magnetic material including, but not limited to, iron oxide and cobalt. The magnetic particles may be contained in polymer beads or micelles having tiny magnetic particles embedded therein. One example of such a polymer bead containing a magnetic particle is commercially available under the trademark Dynabead. Typically, the magnetic particles have a size of from about 10 nanometers to 10 microns.

Magnetic micro-particles attached to biological entities such as biomolecules, cells or viruses act as handles to transmit the magnetic forces. By biological entities or bioentities, we mean any material having a biologic origin including biomolecules, cells, viruses, proteins, peptides, and the like. Using lithography techniques, arrays of such traps are created with nano-scale precision that enable well-defined planar assemblies of micron- or nano-scale magnetic wires to be created such that biological entities such as biomolecules, cells or viruses may be trapped and manipulated on and along the surface of the nano- micro-wires of such arrays. External magnetic fields are provided that can continuously tune the magnetic energy landscape to enable such objects, which on a scale as small as 5-100 nm to 50 microns in size, to be maneuvered along desired trajectories on the platform. The associated field gradients exert magnetic forces that are sufficient to trap and transport particles as small as 5 nm and can exert tunable forces exceeding 100 pN.

The two dimensional landscape of the trap platform enables, (i) joystick or remote manipulation of individual or multiple cells trapped on the array; (ii) the use of a single focal plane for observing magnetic tweezers manipulation with an optical microscope, thereby overcoming need for dynamic refocusing or out-of-focus calibrations that hinder existing magnetic tweezers; (iii) the use of standard lithography techniques to provide easy fabrication of the nano- or micro-wire arrays; (iv) probing nano-scale non-biological entities such as magnetic particles, or probing biomolecules, cells or viruses that have been labeled with or tethered to magnetic particles for use in cellular studies with directed forces; (v) simultaneous measurement of the same experiment on thousands of identical samples enabling the acquisition of statistically valid real time responses; (vi) incorporation of the trap platforms into microfluidic analytical devices to create a new family of on-chip analytic tools to detect small concentrations of one species in the midst of other species; and (vii) rapid sorting of different types of cells from a heterogeneous cell population.

The benefits of a network of mobile magnetic traps include: (a) biological entities such as DNA, cells, viruses or macromolecules can be tethered to the trapped particles on a two dimensional platform and then manipulated using applied electrical and/or magnetic forces; (b) in some embodiments, the micro- or nano-sized particles themselves may be magnetic or be magnetized and manipulated; (c) the application of electric currents to individual wires in the array may be used to move the domain walls along the wires such that the mobile traps could be used, for example, to separate and/or sort sub-populations of cells and/or particles from a larger collection; (d) small magnetic fields, applied in the plane of the wires and/or perpendicular to that plane can be used to manipulate the trapped magnetic particles; and (e) two or more functionalized particles at different locations on the mobile traps may be linked to create a planar magnetic tweezer stage.

The availability of mobile magnetic traps as described herein offers new control that is needed for rapid progress in several branches of science and engineering. In particular, the femto- to pico-Newton scale forces linked to the methods and devices described herein are ideally suited for probing single microparticles and biomolecules in the 10 nm to 100 µm length scales. In physics and chemistry, the methods and devices described herein can provide an understanding of nanoclusters in the transition region between single molecule and microscopic structures where puzzling challenges remain. In biology, the methods and devices described herein can be used to study many vital inter- and intra-cellular processes. Nanoscale engineering will benefit from the options provided by the described methods and devices for organizing, manipulating, and analyzing individual tiny objects. The tunable magnetic trap arrays and methods of use as described herein meet these needs.

Industrial applications which rely on transporting magnetic nanoparticles cover a broad spectrum. The methods and devices described herein have utility in microfluidic devices to manipulate fluid-borne entities inside a network of microscopic channels for clinical diagnosis, forensic applications, and environmental analysis. Specifically, the mobile magnetic traps, used in conjunction with microfluidics channels can be used to separate cells and/or particles of interest from a variety of fluids including blood, plasma, or other body fluids as well as water or other fluid samples. Embodiments of the present invention may also find use in portable devices for environmental and medical analysis.

In accordance with one embodiment, tunable mobile traps are provided along a network of nano- or micro-wires. Such wire networks may be formed using lithography techniques. An example of a form for the wire network is to provide adjacent wires in a zig-zag pattern such that the spacing between adjacent arms of the wire periodically varies. Subsequently, the nano- or micro-wires are magnetized to create domain walls (DW) at the vertices (i.e., bends) in the wires. Magnetic micro- or nano-particles are trapped at the domain walls of the wire network. The domain walls, and the trapped magnetic particles, are moved by introducing electric current through the wires.

In accordance with another embodiment of the present invention, a planar platform may be fabricated to support the network array of nano- or micro-wires and the entrapped magnetic particles. Individual large molecules such as biomolecules, viruses, or polymeric macromolecules can be studied by tethering opposite ends of the molecules to the trapped magnetic particles on adjacent nano-wires. By applying electric current to the network of wires, the magnetic traps are mobilized and can generate stretching, compressive, and/or rotational forces on the tethered molecules as desired. The platform permits real-time observations of single or multiple molecules or other small objects trapped and controllably manipulated in a two-dimensional environment.

According to another embodiment, a magnetic platform is provided and comprises a patterned array of wires positioned on a substrate. The wires have widths ranging from about 100 nanometers to about 10 microns. A plurality of first electromagnets for creating a first magnetic field substantially in the plane of the platform are positioned adjacent the platform. The magnetic field strength ranges from about one (1) Oersted to about five hundred (500) Oersted. An electromagnetic coil for creating a second magnetic field substantially perpendicular to the plane of the platform is also positioned adjacent the platform. A control device is also provided for controlling the application of the first and second magnetic fields. The operation of the control device relies on current or voltage sources which are programmed using software such as LabVIEW software protocols. LabVIEW, from National Instruments, is a commercially available graphical programming software used widely for data acquisition and control. The strength of the trapping force can be tuned using small magnetic fields applied either normal to and/or in the plane of the nano-wire network. This embodiment of the invention enables the transport and assembly of magnetic particles or magnetically labeled biological species solely by the application of magnetic fields.

In a further embodiment of the invention, a process for separating bioentities such as biomolecules, cells or viruses is provided and comprises, flowing a mixture of magnetically labeled and unlabeled bioentities through a first fluid channel, trapping the magnetically labeled entities on a magnetic platform as described above, selectively moving the trap with an electric current, or an external magnetic field, or both, to cause the magnetically labeled bioentities to be transported from the first fluid channel to a second fluid channel, and detaching the magnetically labeled bioentities from the magnetic particle in the second fluid channel.

Accordingly, it is a feature of embodiments of the present invention to provide magnetic array platforms that provide trapping, manipulation, and transport of individual micro- or macro-scale bioentities such as biomolecules, cells, viruses and non-biological magnetic particles. Other features and advantages of embodiments of the present invention will be apparent from the following detailed description, the accompanying drawings, and the appended claims.

BRIEF DESCRIPTION OF THE SEVERAL VIEWS OF THE DRAWINGS

The following detailed description of specific embodiments of the present invention can be best understood when read in conjunction with the following drawings, where like structure is indicated with like reference numerals and in which.

DETAILED DESCRIPTION

Embodiments of the invention enable the manipulation of micro- and nano-scale particles. In one embodiment, tunable mobile traps are provided in magnetic nano- or micro-wire networks. These traps are moved along said wires by passing electric current through the wires The current-driven mechanism also enables particles trapped on a specific wire within an array of wires to be targeted and manipulated. The application of electric current to the mobile traps provides a continuously tunable environment for examination of biological entities such as biomolecules, cells, viruses which have been labeled with or tethered to magnetic particles and micro- or nano-scale magnetic particles.

In another embodiment, micro- and nano-scale particles are manipulated by the application of suitable external magnetic fields to a network of wires arrayed on a platform. For example, the particles can be transported by applying a magnetic field in the plane of the platform as the strength of the trapping force is tuned via small magnetic fields applied normal to the wire network plane.

Figure 1A:
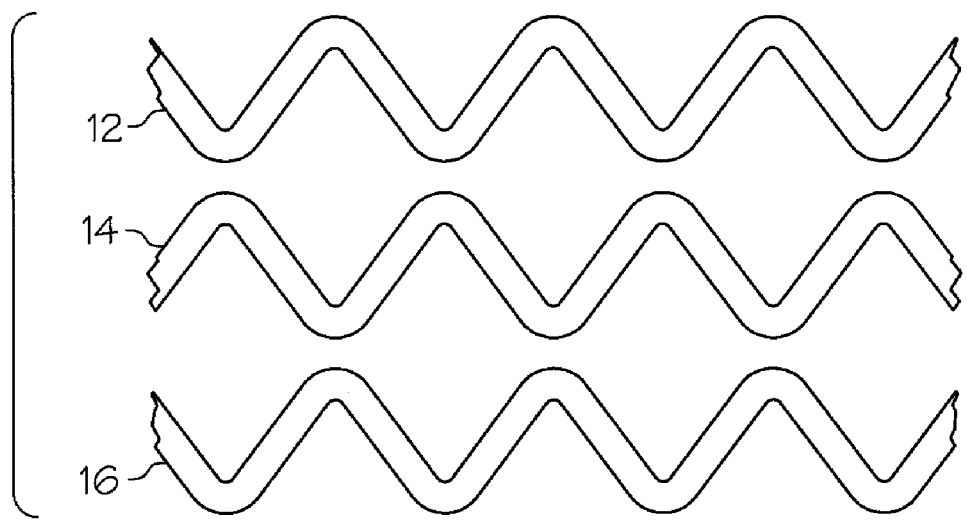
FIG. 1A is a schematic illustration of mobile magnetic traps in a nano- or micro-wire network.
Figure 1B:
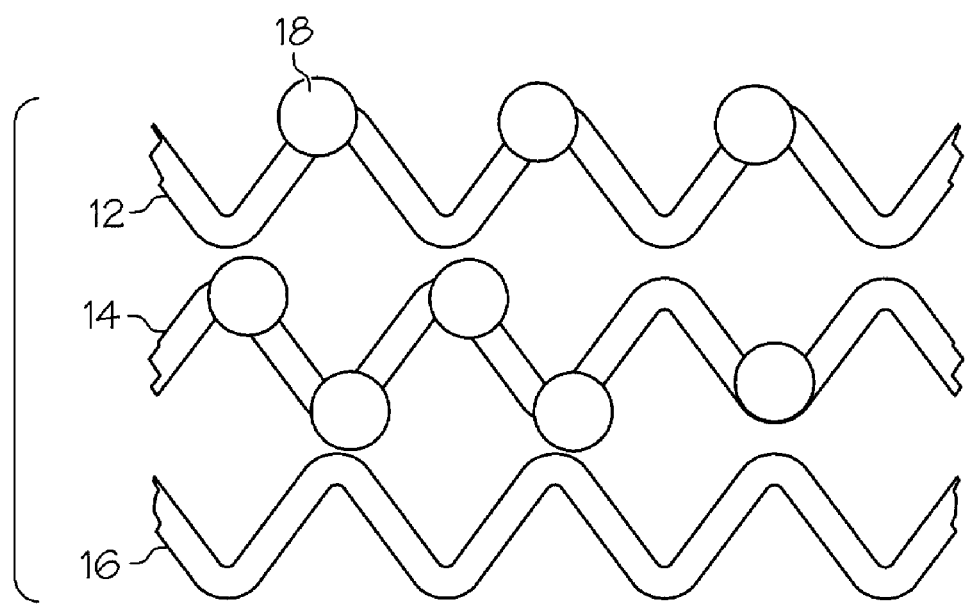
FIG. 1B is a schematic illustration of magnetic micro- or nano-particles trapped at domain walls at vertices of the nano- or micro-wire network.
Figure 1C:
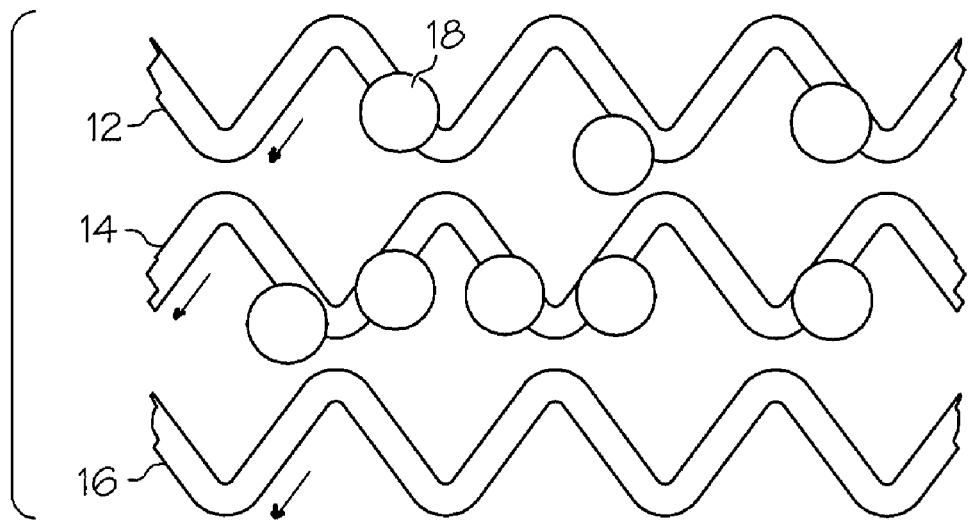
FIG. 1C is a schematic illustration of the movement of the trapped magnetic particles effected by passing electrical current through the nano- or micro-wire network.

Schematic illustrations of the mobile magnetic traps are shown in FIGS. 1A through 1C. As shown in FIG. 1A, a nano- or micro-wire network array with wires 12, 14, and 16 is fabricated using lithography techniques that are known in the art. These wires that are produced may be in the form of a two-dimensional array of adjacent zig-zag patterns as shown. The bends (vertices) in the wires may be matched so that the spacing between adjacent wires varies along respective lengths of wire.

Figure 1D:
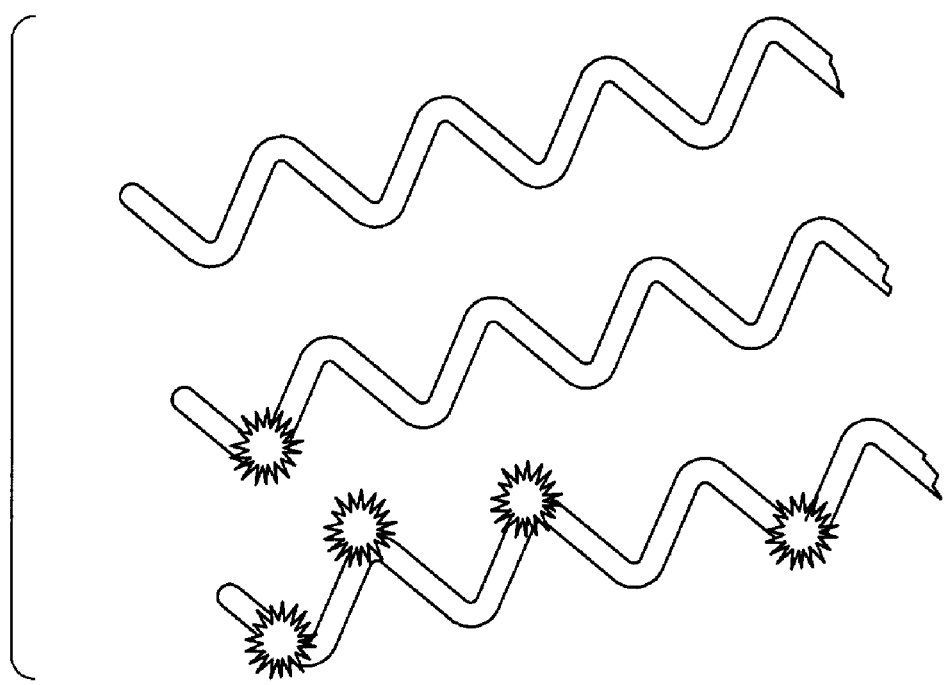
FIG. 1D is a schematic illustration of five one micrometer diameter magnetic beads trapped at the vertices of one micrometer diameter wires.

After fabrication, the wires are magnetized to create domain walls (i.e., interfaces separating magnetic domains) at the vertices of the wires. As shown in FIG. 1B, magnetic micro- or nano-particles 18 are trapped at domain walls at the vertices between adjacent wires in the network array. As shown in FIG. 1C, electric current is passed through the wires in the direction shown by the arrows, causing the trapped magnetic particles 18 to move along respective ones of the wires. FIG. 1D shows a schematic illustration of five one micrometer diameter magnetic beads trapped at vertices of one micrometer wide wires.

Figure 2A:
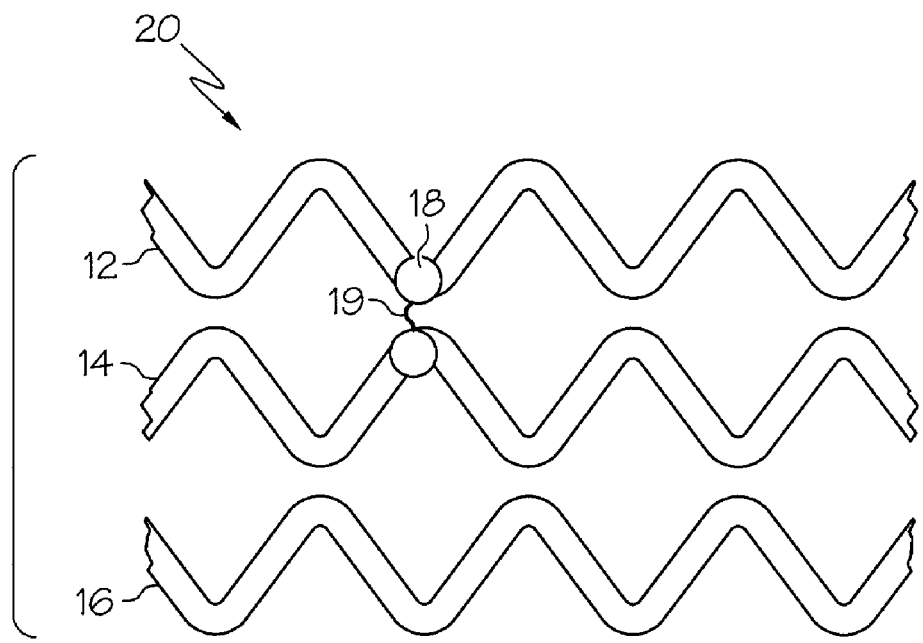
FIG. 2A is a schematic illustration of a DNA strand tethered at opposite ends of the strand to two trapped magnetic beads in a nano-wire network.
Figure 2B:
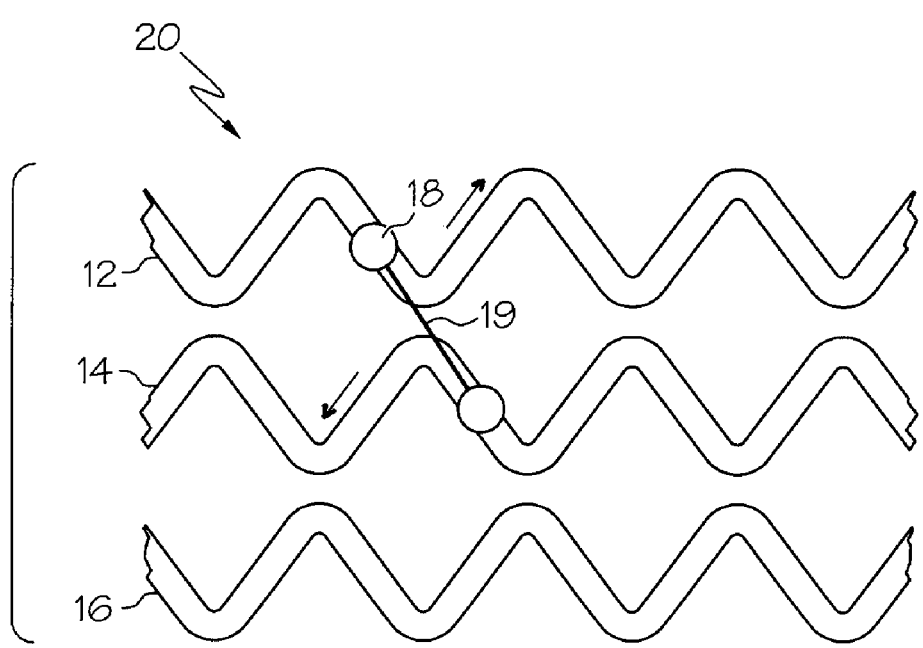
FIG. 2B is a schematic illustration of the passage of current through the nano-wire network to effect movement of the magnetic beads which in turn cause stretching of the tethered DNA strand.

In another embodiment as shown in FIGS. 2A and 2B, a planar platform 20 for supporting a network of wires 12, 14, and 16 is fabricated using a suitable substrate such as silicon. As previously, discussed, known lithography techniques may be utilized to construct the array of nano- or micro-wires in, for example, a zig-zag pattern as shown. The wires are magnetized, and small magnetic particles or beads 18 are then trapped at domain walls at the vertices of adjacent wires. Large molecules can be tethered to the magnetic particles using known chemical techniques. For example, large molecules such as biomolecules including DNA, proteins, or viruses can then be captured and held in these traps. By tethering the molecules at opposite ends thereof, the molecules can be manipulated by the application of electric current to cause the magnetic particles to move along respective wires in the network. As further discussed in paragraph [0042] below, this movement of the magnetic particles will provide compressive, stretching or rotational forces on the tethered biomolecule.

As will be understood, the design and architecture of the network of nano- or micro-wire arrays enable different trapping site configurations to be fabricated. This permits the fabrication of two-dimensional platforms having different wire layouts for trapping micro- or nano-sized magnetic particles at specific locations. Such platforms enable the study of magnetically labeled or tethered individual molecules such as DNA, viruses, proteins, and polymeric macromolecules, the interactions between such large molecules, and the response of such molecules to external stimuli.

A platform of this design has the potential to study and deliver individual entities such as biomolecules, cells or viruses to specific locations. This capability has the potential for improvements in the diagnosis, and personalized health treatment, of a variety of health conditions. Another use for such a platform would be to tag DNA molecules or cells with different biomarkers on a platform to study their response to various stimuli.

A schematic illustration of opposite ends of a DNA strand 19 tethered to two trapped magnetic beads 18 is shown in FIGS. 2A and 2B. The magnetic beads are trapped at the domain wall localized at adjacent vertices on two separate wires A and B that have been magnetized to create such domain walls at their respective vertices. The application of electric currents through the wires in the directions shown by the arrows drives the domain walls along the wires. Movement of the trapped beads in response to the current causes the tethered DNA strand to be stretched. The trapped magnetic beads can be driven back to the original positions by reversing the current flow, thereby compressing the strand. The platform enables real time observations of single or multiple objects trapped and controllably moved within a two-dimensional landscape.

The prior art has attempted several approaches to manipulate magnetic particles. While external magnetic field gradients, such as those created through micro-coils and current lines, are often effective, they are of limited value when targeting individual small magnetic objects within an array. Recently the magnetic domains in ferrite garnet films were used to assemble and guide colloidal particles. Despite the relative ease of moving the domain wall (DW) with an external magnetic field in bulk systems, as dimensions shrink however, it becomes increasingly difficult to control with macroscopic external fields, the individual wall response within an array. This difficulty is alleviated in the present application by the passage of current through specific wires to move the domain walls and associated trap.

Embodiments of the present invention take advantage of localized magnetic field gradients that originate from a domain wall (~10s-100s nm wide) within designed structures, to function as a tunable trapping potential. Furthermore, electric current and spin-torque physics are used to reorient the magnetic moments and move domain walls and their associated fields by a spin-polarized current. This spin torque phenomenon has been demonstrated in a current-in-plane (CIP) configuration where polarized electrons passing through a domain-wall (DW) pushed the wall in the direction of electron flow.

Since movement of a DW involves reorienting the magnetization vector, a domain wall traveling in narrow channels is accompanied by the emanating magnetic field that tracks along with the wall. As shown in paragraphs [0049] and [0050] below, the associated field gradients exert magnetic forces that are sufficient to trap particles as small as 5 nm and can exert forces exceeding 300 pN. Each trap therefore acts as a quasi three-dimensional potential energy well for a tiny object.

The fabrication of an entire array of these magnetic traps, provides an extended potential energy landscape whose symmetries and architecture can be easily designed. Static trapping arrays and landscapes are useful in manipulating microscopic objects such as biological cells that have been labeled with or tethered to magnetic particles and organizing them into useful and interesting configurations. Steering these traps with spin polarized current therefore provides the framework to not only study how different individual particles can be maneuvered along predetermined paths, but also how they move through the landscapes when driven by other external forces.

As discussed in paragraph [0036] above, the application of suitable external magnetic fields permits the magnetic traps to be moved, causing particles trapped therein to be transported as well. The strength of the trapping force applied to the particles can be tuned by the use of a small external magnetic field applied normal to the plane of the array.

Figure 3:
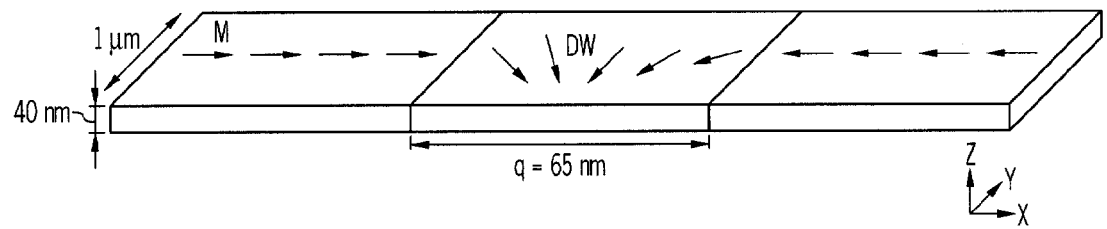
FIG. 3 is a schematic illustration of head-to-head magnetic domain walls (DW) of width 65 nanometers for example within a magnetic channel.

To estimate the field, forces, and trapping potential associated with a domain wall, a 1 μm×40 nm CoFe channel supporting a head-to-head wall of width q=65 nm (FIG. 3) was considered. The force $F=\nabla(m.B)$, where $m \propto B$ is the magnetic dipole moment of a single paramagnetic bead in a magnetic field B. The arrows in FIG. 3 indicate the magnetization direction.

Figure 4A:
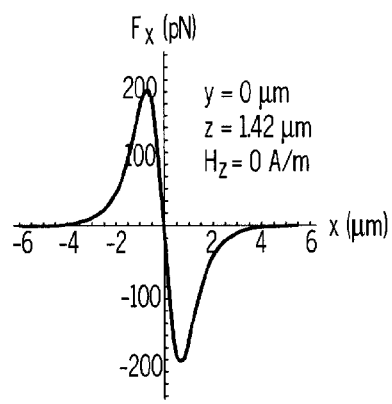
FIG. 4A is a graph of domain wall generated forces, $F_x$, (in plane) on a magnetic bead (x=0.85) lying 1.42 μm above the domain wall.
Figure 4B:
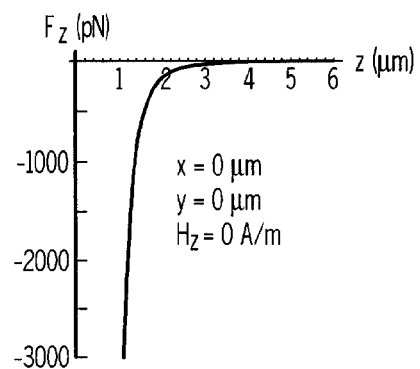
FIG. 4B is a graph of domain wall generated forces, $F_z$, (axial) perpendicular to the platform on a magnetic bead (x=0.85) lying 1.42 μm above the domain wall.
Figure 4C:
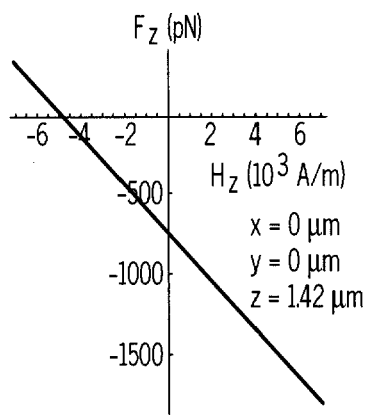
FIG. 4C is a graph of the variation of axial force, $F_z$, as a function of external magnetic field, $H_z$, directed along the z direction.
Figure 4D:
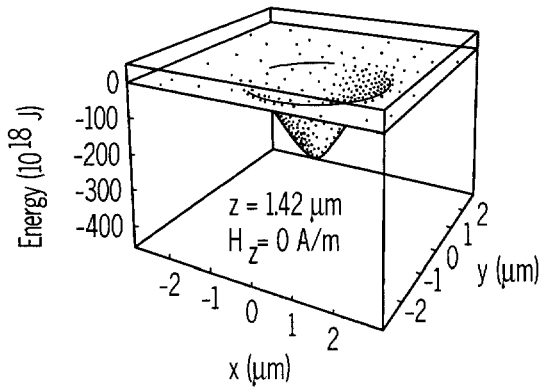
FIGS. 4D-4F are graphs illustrating the variation of potential energy profiles with small external fields, $H_z$, where in FIG. 4D, $H_z$=0, in FIG. 4E, $H_z$=1000 A/m directed from wire to magnetic bead; and in FIG. 4F, $H_z$=−1000 A/m (1 Oe=79.6 A/m) directed away from wire towards bead; the zigzag wire lies on the X-Y plane with the vertex located at X=0, Y=0.
Figure 4E:
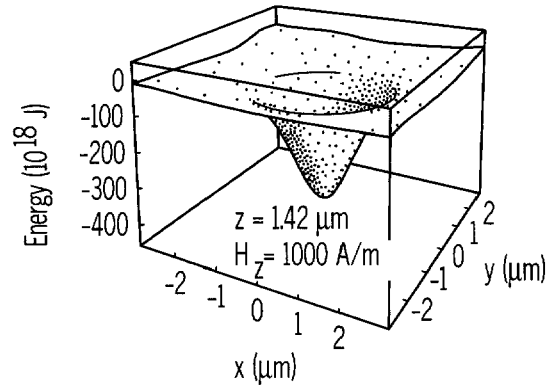
Figure 4F:
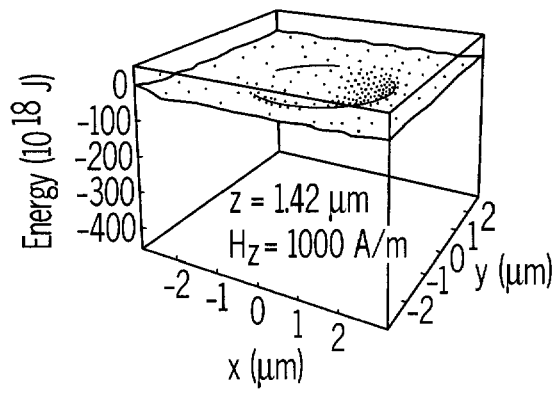

As shown in FIGS. 4A and 4B, domain wall generated forces are designated as $F_x$, for in-plane forces and $F_z$, for axial forces, on a magnetic bead (x=0.85) lying 1.42 μm above the domain wall. The negative values shown in FIG. 4B indicate an attractive force directed toward the domain wall. FIG. 4C shows the variation of axial force, $F_z$, as a function of external magnetic field $H_z$ directed along the z-axis. FIGS. 4D through 4F show the variation of potential energy profiles with small external magnetic fields H. In FIG. 4D, the external field, Hz=0. In FIG. 4E, the external field Hz=1000 A/m directed from the wire to the magnetic bead (where 1 Oe=79.6 A/m). In FIG. 4F, the external field Hz=1000 A/m directed away from the wire towards the bead.

Several features of embodiments of the invention are demonstrated in the graphs illustrated in FIGS. 4A through 4F. In FIG. 4A, in-plane magnetic forces, $F_x$, are directed toward the origin, i.e., those forces localize particles toward domain wall center. FIG. 4B shows that, in the region directly above the domain wall, the magnetic field is dominated by the z-component of the magnetic field. Additionally, $F_z$, the force directed normal to the wire, is strongest above the domain wall center and directed toward the channel. Thus, that force traps the magnetic particle in the vicinity of the domain wall. For a value of z approximately equal to 1 μm, the magnitude of $F_z$ is hundreds of pico-Newtons (pN).

As shown in FIG. 4C, the trapping forces can be tuned in both magnitude and direction by a small external magnetic field, $H_z$ (10's of Oe), oriented normal to the wire. The net magnetic force is attractive or repulsive, enabling the trapped magnetic particle to be localized at tunable distances above the domain wall. Finally, the energy profiles shown in FIGS. 4D through 4F show the ability to tune the trapping potential with an external magnetic field ($H_z$) and to move the trap across the platform of wires.

These results demonstrate the ease of creating magnetic domains with a planar array design which enables domain walls to be reproducibly created at predetermined locations along a nano- or micro-wire array. The design, architecture, material parameters, and structural dimensions of the magnetic channels determine the specific trapping sites, domain wall profile, widths, and field gradients. Magnetic particles, with and without tethered biological entities, can be trapped at domain walls. The architecture of the wire patterns promotes coupling of adjacent trapped particles through specific molecular links. This transverse magnetic tweezer system based on a planar nano- or micro-wire network provides real-time observation and analysis of single or multiple inert as well as biological objects trapped and moved within a two-dimensional landscape.

Figure 5:
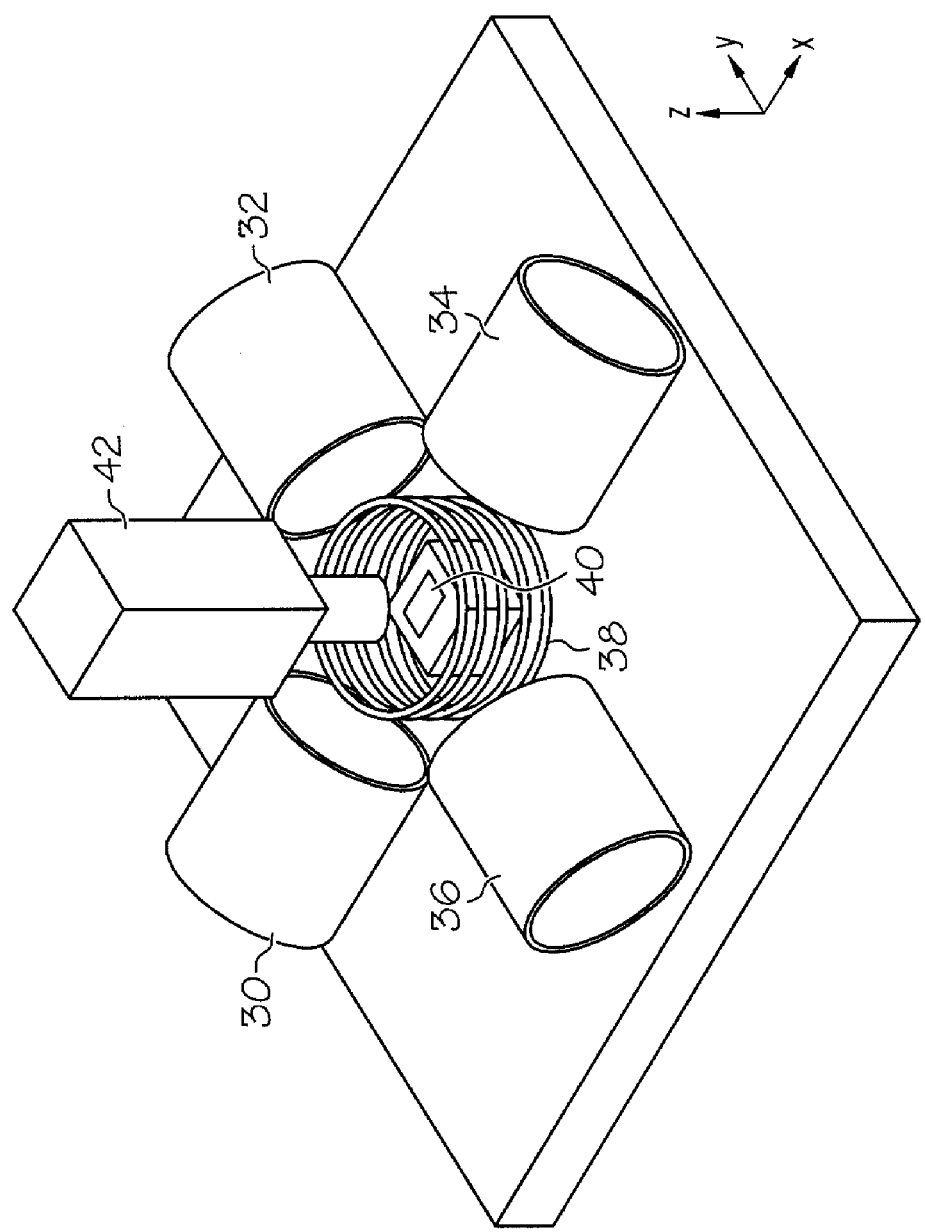
FIG. 5 schematically illustrates a system used to manipulate magnetic particles in both in-plane and out-of-plane directions.

In another embodiment, the platform can be used to remotely transport biological entities using a magnetic field alone. A series of nano-wires, arranged in an array at specific co-ordinates on the platform substrate, offers the ability to create a programmable platform to transport a biological entity such as a cell to a given coordinate on the surface of the platform. In one form, the external in-plane field $H_{//}$ is created by four orthogonally spaced miniature electromagnets 30, 32, 34, and 36, while a perpendicular field, $H_z$, is produced by a coiled loop 38 as illustrated schematically in FIG. 5. By remotely switching the direction of the perpendicular field between out-of-plane and into-plane orientations, as well as rotating the in-plane magnetic field, magnetically labeled biological entities such as sample 40 can be moved to a specific location on the planar array. When a specific final destination for transporting a given cell has been identified, the external magnetic field can be programmed to transport it to that specific site. The programming can be achieved, for example, by using LabVIEW protocols. The process can be viewed by an optical microscope 42 or other suitable instrument.

Figure 6:
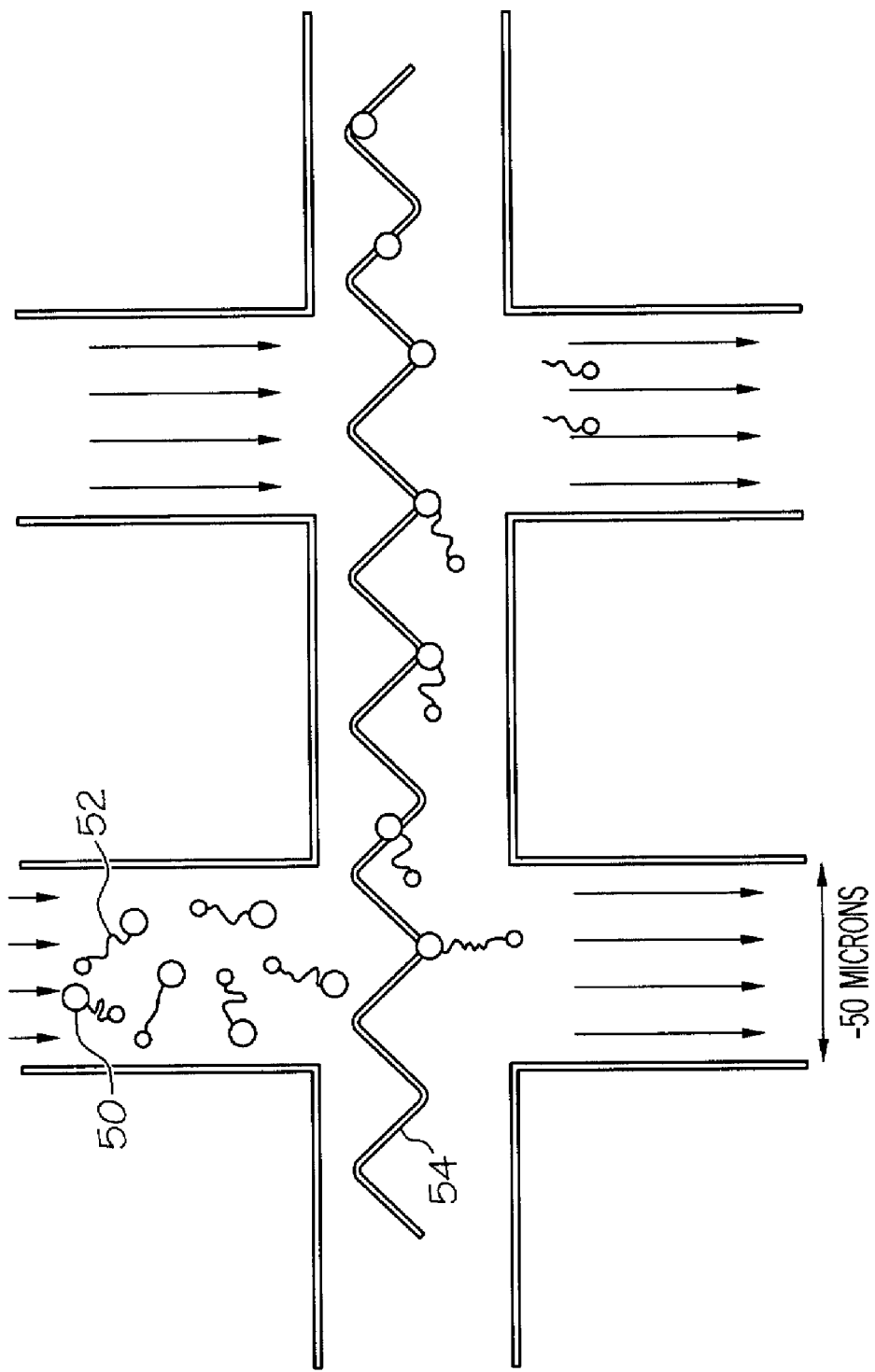
FIG. 6 schematically illustrates the operation of a microfluidic platform used for biomolecular separation.

The magnetic platform can also be used as an analytical device by embedding the platform within a channel of a microfluidic device as depicted schematically in FIG. 6. Microfluidics, which deals with the control and manipulation of fluid-borne entities that are geometrically constrained to the micron scale, is emerging as an important single chip analytic tool. The advantages include increased resolution, faster response, smaller sample sizes, and increased parallel analysis. However, conventional microfluidic devices can be overwhelmed in the detection of small concentrations of one species in the midst of other species.

A schematic of a microfluidic platform for separation of micro- or nano-scale magnetic particles 50 and tethered biological entities 52 such as biomolecules, cells or viruses is shown in FIG. 6. The device incorporates the isolated magnetic elements whose strong magnetic field gradients can be used to trap and transport the cells. The method is attractive because it relies on the high cell separation selectivity of the magnetic elements. In operation, an embedded magnetic trap array 54 in one microfluid channel is used to trap magnetically labeled species 50-52 in the sample flowing in a channel perpendicular to the array channel. Subsequently a transfer method such as those techniques based on the passage of electrical current as described above in paragraph [0035] or the application of external magnetic fields as described above in paragraph [0036], can move the conjugated species to a separate cross channel where the species 52 can be chemically detached from magnetic particles 50 and detected. As illustrated in FIG. 6, magnetic platforms as described above can be readily blended into existing microfluidic technology as the basis for a new family of on-chip analytic tools.

Embodiments of the present invention may find use in industrial applications in which magnetic nanoparticles are transported. Examples of such applications include microfluidic devices that manipulate fluids and fluid-borne entities inside a network of microscopic channels for clinical diagnosis, forensic applications and environmental analysis. The magnetic microparticles can be used as magnetic inks for sensing. Embodiments of the invention may also find use in portable medical and environmental analysis devices.

The mobile magnetic traps provide the control needed for the manipulation of single biological entities. In particular, the femto- and pico-Newton scale forces that are created are well suited for probing single microparticles and biological entities such as biomolecules, cells and viruses having sizes in the 10 nm to 100 µm size range. Tunable magnetic traps as embodied herein offer many ways to organize, manipulate and analyze individual small objects on a cellular or smaller scale.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A mobile magnetic trap comprising, a plurality of nano- or micro-wires positioned on a planar substrate such that each of said wires includes one or more non-linear segments such that the spacing between individual wires varies along the respective lengths of said wires or one or more linear segments which include narrowed sections or notches along their respective lengths; said wires being magnetized to form domain walls at respective vertices of said non-linear segments or narrowed sections or notches along the length of said linear segments; and a source of electric current connected to said plurality of wires to move said domain walls along each of said wires and transport magnetic particles, or magnetically labeled or magnetic biological entities, trapped by said domain walls.

2. A mobile magnetic trap as claimed in claim 1 in which said wires include non-linear segments in a zigzag pattern.

3. A mobile magnetic trap as claimed in claim 1 in which said wires include non-linear segments in a stair-stepped pattern.

4. A mobile magnetic trap as claimed in claim 1 wherein each of said wires includes one or more linear segments having narrowed sections or notches along each of their respective lengths, said narrowed sections or notches forming said magnetic traps.

5. A mobile magnetic trap as claimed in claim 1 including a magnetic field source.

6. A mobile magnetic trap as claimed in claim 4 in which said magnetic field source comprises a plurality of electromagnets positioned to create a magnetic field substantially in the plane of said nano- or micro-wires.

7. A mobile magnetic trap as claimed in claim 5 in which said magnetic field source comprises an electromagnetic coil or electromagnet positioned to create a magnetic field substantially perpendicular to the plane of said nano- or micro-wires.

8. A mobile magnetic trap as claimed in claim 1 including magnetic particles positioned at one or more of said domain walls.

9. A mobile magnetic trap as claimed in claim 8 in which said magnetic particles comprise polymer beads or micelles having a magnetic material embedded therein.

10. A mobile magnetic trap as claimed in claim 9 in which said magnetic particles have a diameter of between about 10 nanometers to about 10 microns.

11. A mobile magnetic trap as claimed in claim 1 in which said substrate comprises silicon, silica oxide-based glass, metal oxide, or combinations thereof as well as other materials on which said nano- or micro-wires can be fabricated.

12. A mobile magnetic trap comprising, a plurality of nano- or micro-wires positioned on a planar substrate such that each of said wires includes one or more non-linear segments such that the spacing between individual wires varies along the respective lengths of said wires or one or more linear segments which include narrowed sections or notches along their lengths; said wires being magnetized to form domain walls at respective vertices of said non-linear segments or at said narrowed sections or notches of said linear segments; a plurality of first electromagnets for creating a first magnetic field substantially in the plane of said substrate; an electromagnetic coil or electromagnet for creating a second magnetic field substantially perpendicular to the plane of said substrate; and a control device for controlling the application of said first and second magnetic fields to transport magnetic particles, or magnetically labeled or magnetic biological entities, trapped by said domain walls to any location on said substrate.

* * * * *

UNITED STATES PATENT AND TRADEMARK OFFICE
CERTIFICATE OF CORRECTION

PATENT NO. : 8,399,229 B2  
APPLICATION NO. : 12/950130  
DATED : March 19, 2013  
INVENTOR(S) : Ratnasingham Sooryakumar et al.

Page 1 of 1

It is certified that error appears in the above-identified patent and that said Letters Patent is hereby corrected as shown below:

In the Specification

Col. 8, Line 16, "H." should read --$H_z$--.

Signed and Sealed this  
Fifth Day of November, 2013

Teresa Stanek Rea  
*Deputy Director of the United States Patent and Trademark Office*